Figure 1:
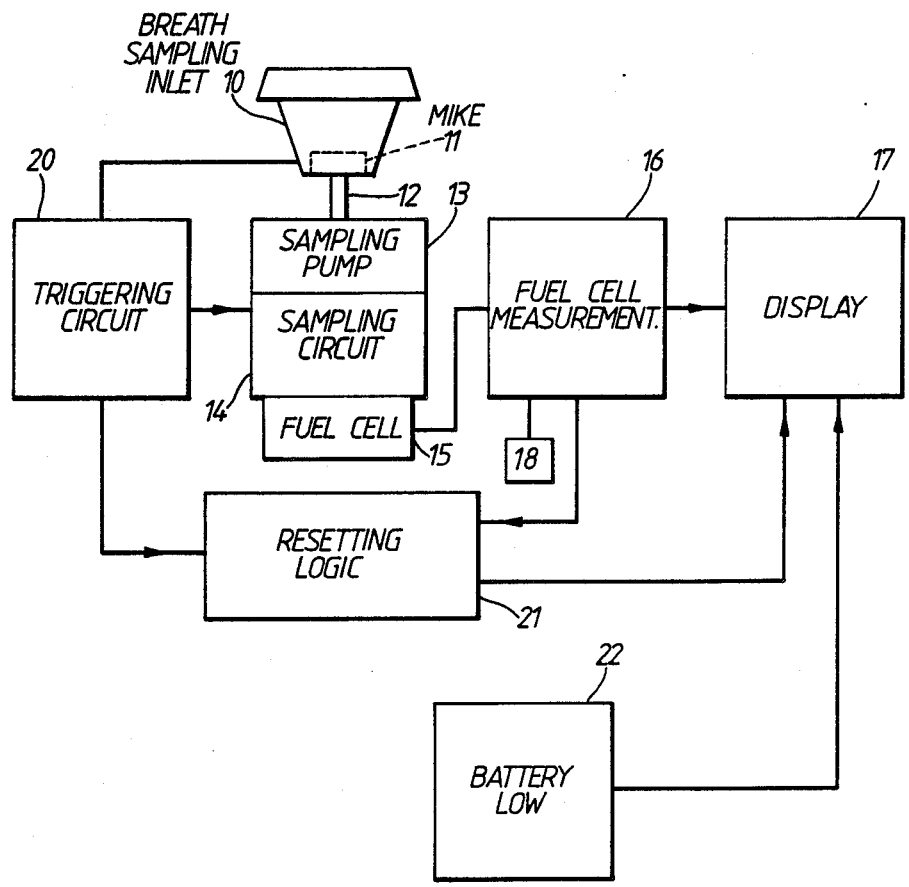

United States Patent [19]
Jones

[11] Patent Number: 4,868,545
[45] Date of Patent: Sep. 19, 1989

[54] ALCOHOL OR DRUGS BREATH DETECTING DEVICES

[75] Inventor: Thomas P. Jones, Sully, United Kingdom

[73] Assignee: Lion Technology Limited, Barry, England

[21] Appl. No.: 154,252
[22] PCT Filed: Jun. 12, 1987
[86] PCT No.: PCT/GB87/00412
§ 371 Date: Jan. 28, 1988
§ 102(e) Date: Jan. 28, 1988
[87] PCT Pub. No.: WO87/07723
PCT Pub. Date: Dec. 17, 1987

[30] Foreign Application Priority Data
Jun. 14, 1986 [GB] United Kingdom ............... 8614515

[51] Int. Cl.⁴ ............................................. G08B 23/00
[52] U.S. Cl. ...................................... 340/573; 73/23
[58] Field of Search ............... 340/573; 73/23, 27 R, 73/864; 128/719; 422/84

[56] References Cited
U.S. PATENT DOCUMENTS
3,858,434 1/1975 Hoppesch et al. .................. 73/23
4,749,553 6/1988 Lopez et al. ..................... 73/23 X Primary Examiner—Jerry W. Myracle
Attorney, Agent, or Firm—Young & Thompson

[57] ABSTRACT

Apparatus for detecting the presence of alcohol in expired breath in the atmosphere, comprising a gas sampler, a detector for the presence of alcohol in a gas sample, an output indicator or recorder coupled to the detector to provide an output signal when alcohol is detected, and an automatic controller for actuating the sampler and detector in response to a signal from a sensor arranged to be responsive to the presence of a subject to be tested.

19 Claims, 9 Drawing Sheets

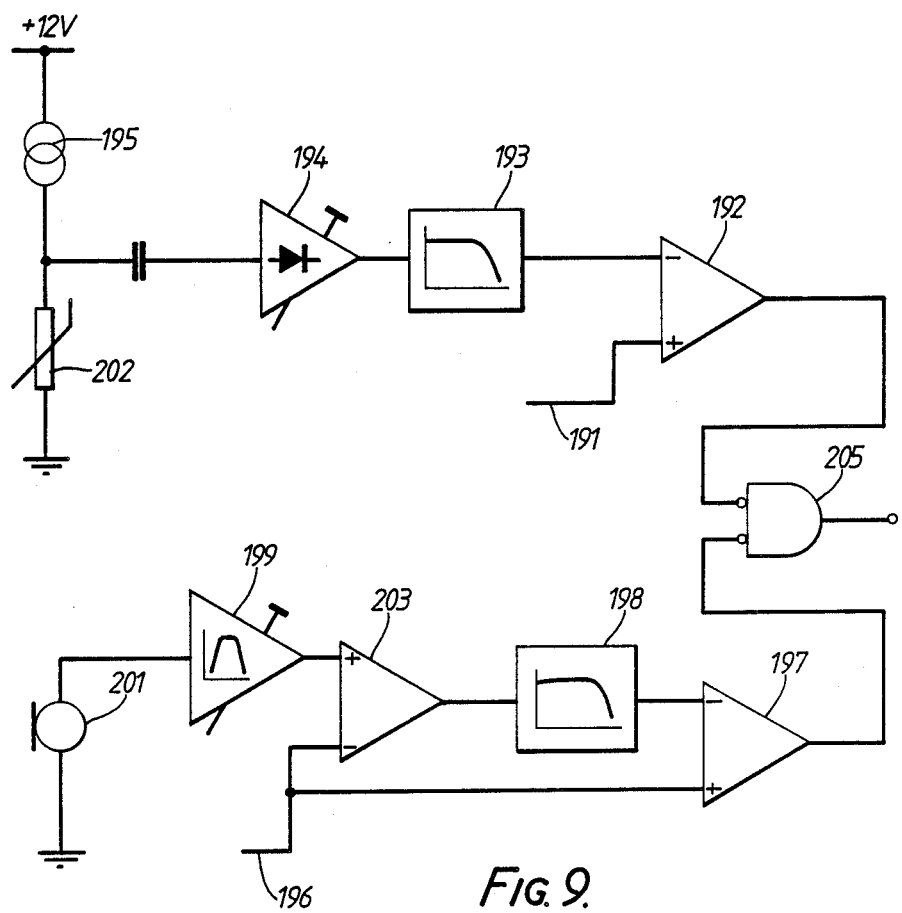
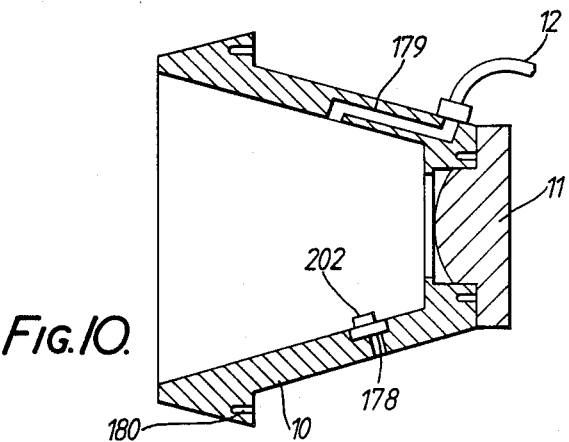
FIG. 9.
FIG. 10.

ALCOHOL OR DRUGS BREATH DETECTING DEVICES

This invention relates to apparatus for detecting alcohol or drugs in exhaled breath and is particularly applicable in situations where one or more people are expected to pass or remain in or adjacent a particular position, or where a person is required to speak into a telephone or radio transmitter for example. This may apply for instance to crowds entering a football ground, or a railway station, bus station, school, cinema, prison, place of public entertainment, transport, a high security zone, or the like.

The invention may also be applicable to any situation where a subject is required to speak into a microphone, for example when using a telephone, or radio transmitter, and can thus be applied to instruments designed to monitor subjects in "home arrest" or "parole" situations.

In some applications the system must be capable of operating effectively to take a large number of tests at short intervals and it is wholly inappropriate to expect each person tested to breath into a breathing tube. Accordingly it is desirable in such applications that the apparatus should be capable of operating at some distance from the suspect's mouth, but nevertheless it requires some control or indication of the distance involved in order to provide a reasonably accurate test result.

Broadly stated from one aspect the invention consists in apparatus for detecting the presence of alcohol or drugs in expired breath in the atmosphere, comprising a gas sampler, a detector for the presence of alcohol or drugs in a gas sample, an output indicator or recorder coupled to the detector to provide an output or "drugs" signal when alcohol or drugs are detected, and an automatic controller for actuating the sampler and detector in response to a signal from a sensor arranged to be responsive to the presence of a subject to be tested.

According to a preferred feature of the invention the sensor is responsive to speech, or noise level, or fluctuation, or movement, temperature, pressure, mass, body weight, or an interruption in a radiated beam, or a combination of any two or more such "proximity" or "presence" parameters.

Conveniently the sensor includes a microphone responsive to speech at a predetermined acoustic level, and the microphone may be combined with filters or other circuitry designed to respond to frequency range or pattern or volume of the human voice, and/or to the temperature range of human breath. In a particular preferred arrangement the microphone produces a "speech signal" and the apparatus also includes a proximity sensor sensitive to the presence of a human body and producing a "proximity signal" and means for detecting a simultaneous or concurrent combination of both signals. The proximity sensor may, for example, be a temperature responsive element positioned close to the acoustic transducer, and combined with circuitry designed for example to make the sensor independent of changes in ambient temperature.

In any case the alcohol detector preferably comprises an electrochemical fuel cell and means for measuring or detecting the output of the cell to provide an indication of the alcohol content in the sample and the gas sampler comprises a pump for drawing or impelling a gas sample, preferably of predetermined volume, into contact with the detector. The pump is preferably electrically operated and includes a control circuit incorporating a pump, and in order to operate at short intervals the gas sampler and detector preferably incorporate a heater and a temperature control. If the alcohol detector comprises an electrochemical fuel cell it may be desirable to "clear the cell" between tests and to accelerate this the apparatus may include means for short circuiting the cell between tests. Alternatively the cell may be operated on a transresistance amplifier for example, and effectively on continuous short circuit.

In a particular preferred construction the apparatus includes a microphone acting as an acoustic transducer sensitive to speech, and an air temperature responsive element located immediately adjacent thereto, the microphone and temperature sensing element being coupled through a logic circuit to the output. Both the microphone and temperature are conveniently located in or adjacent to a cone or cup designed as a microphone mouthpiece. The temperature sensing element is preferably incorporated into circuitry designed to sense fluctuations in the output caused by air turbulence, and in that way to act as a "proximity sensor".

The apparatus may also include an audible or visible sign or signal to notify the subject that he should stand closer to the speech detector, this being operated automatically by the proximity detector.

The apparatus may also incorporate a delay device arranged to impose a short delay on the operation of the breath sampler or pump, to ensure that optimum breath conditions are achieved before the sample is taken.

Figure 2:
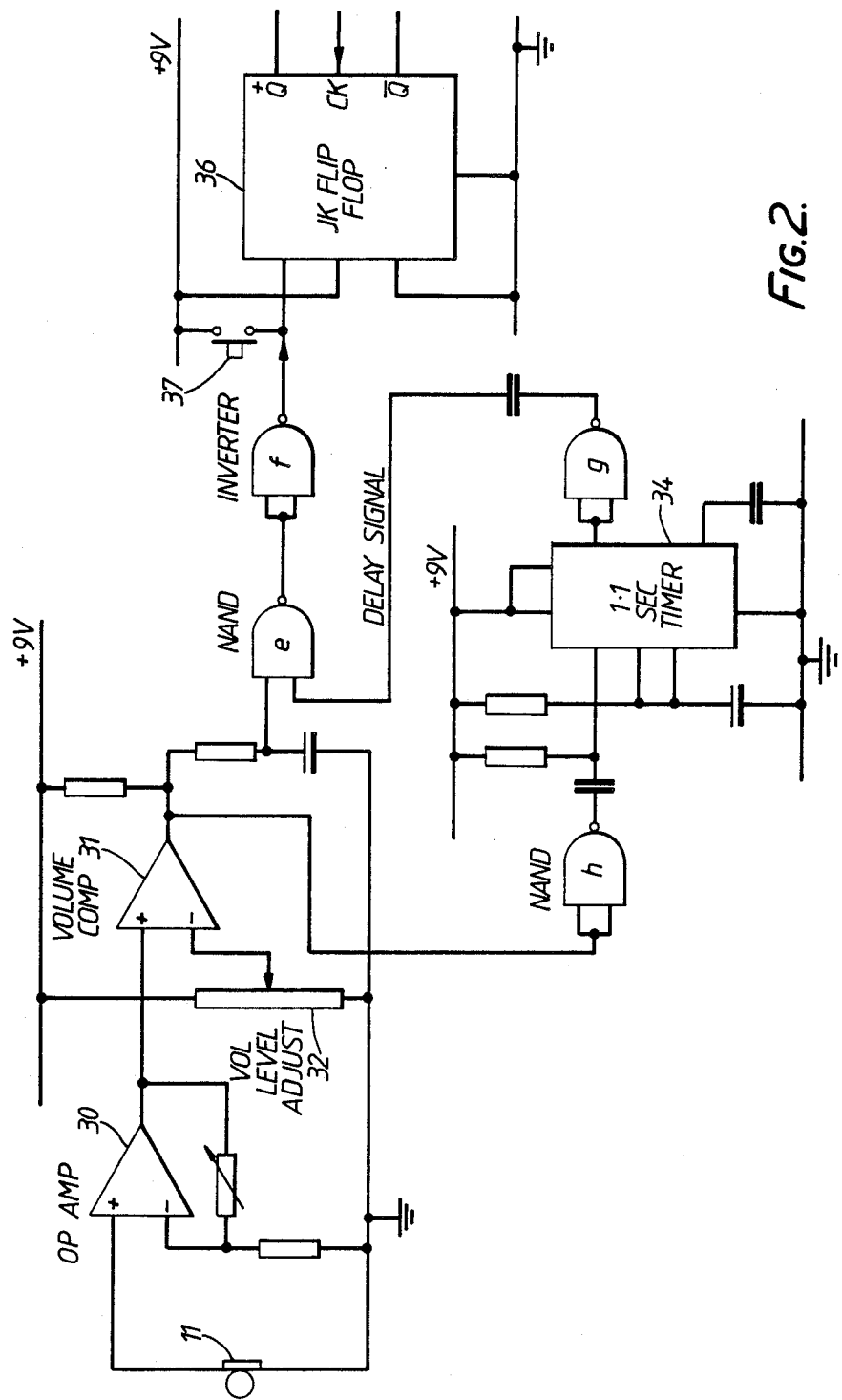
Figure 3:
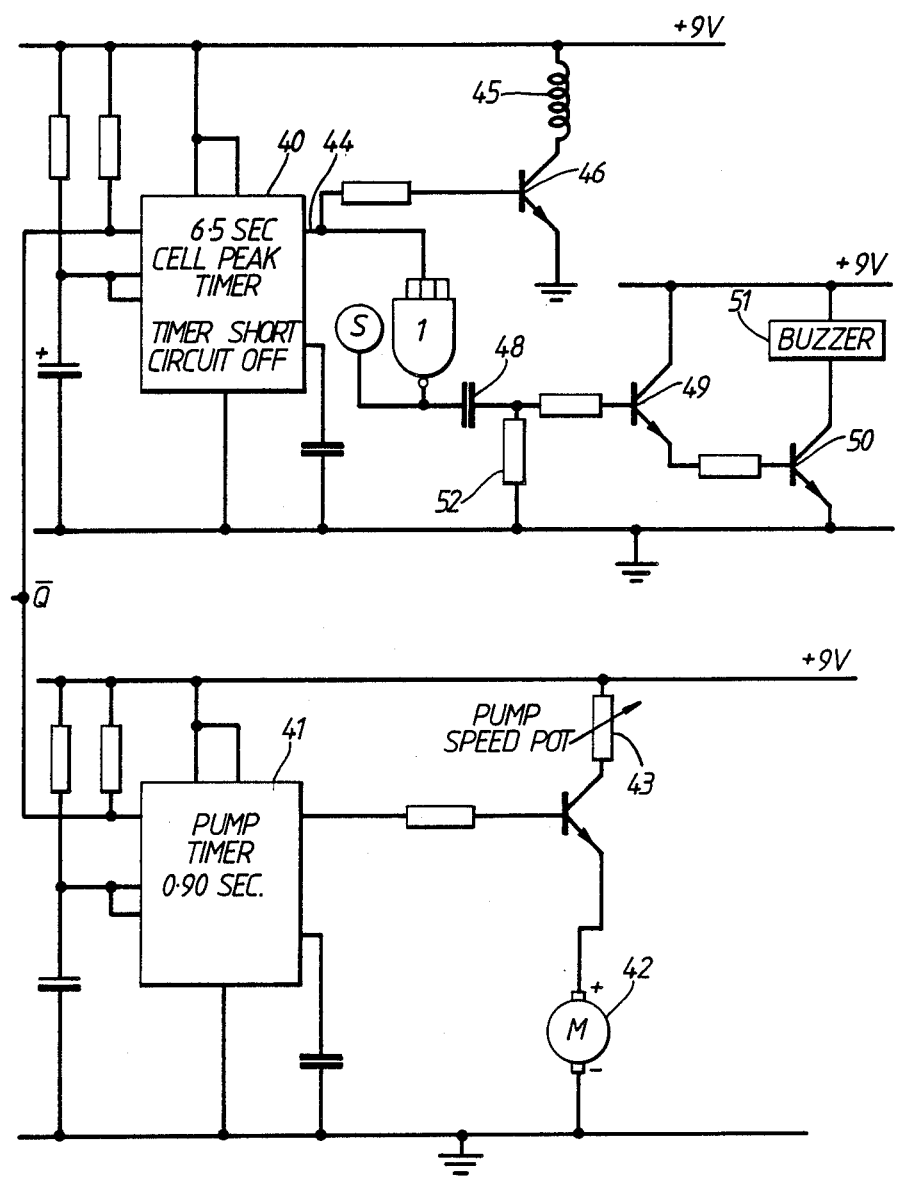
Figure 4:
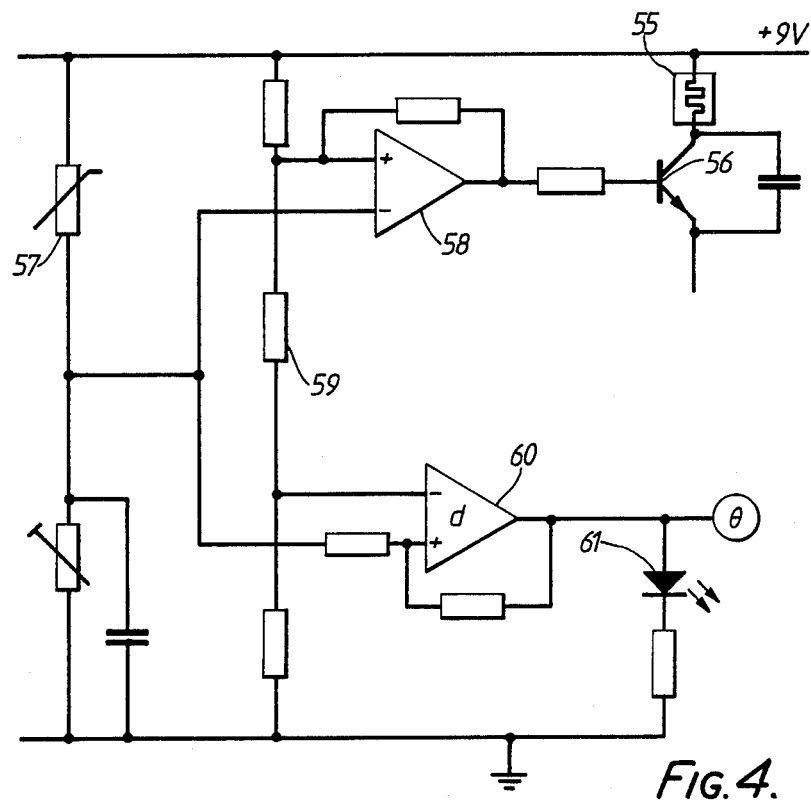
Figure 5:
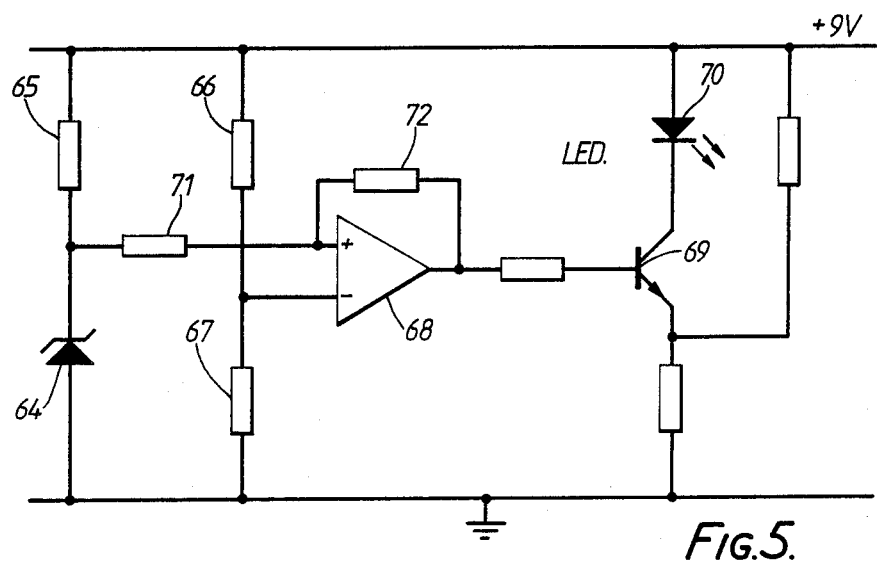
Figure 6:
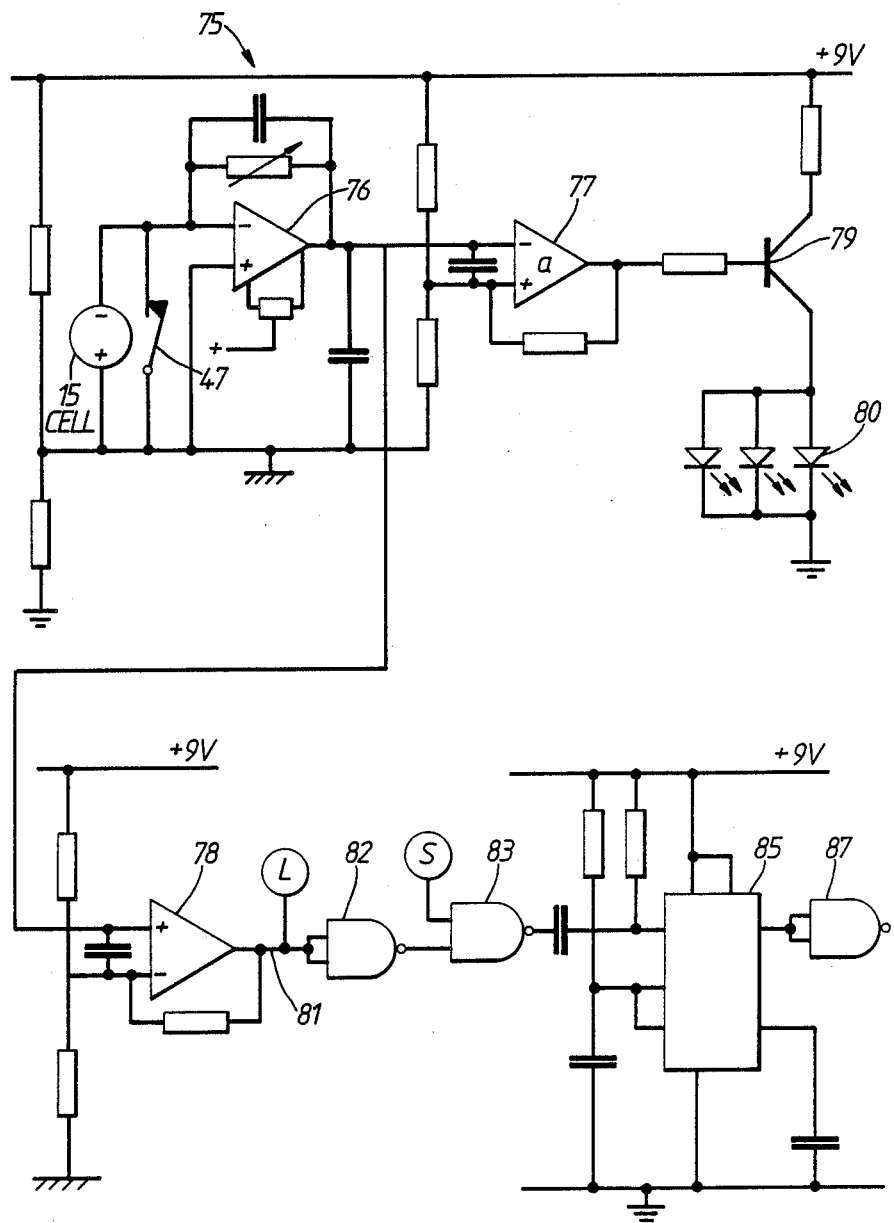
Figure 7:
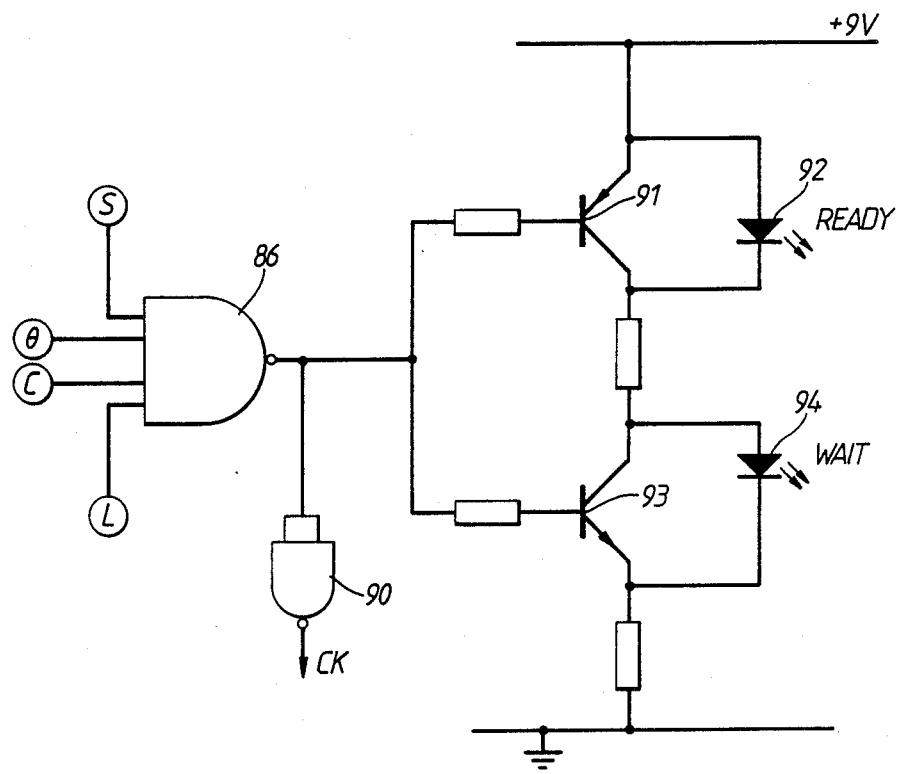
Figure 8:
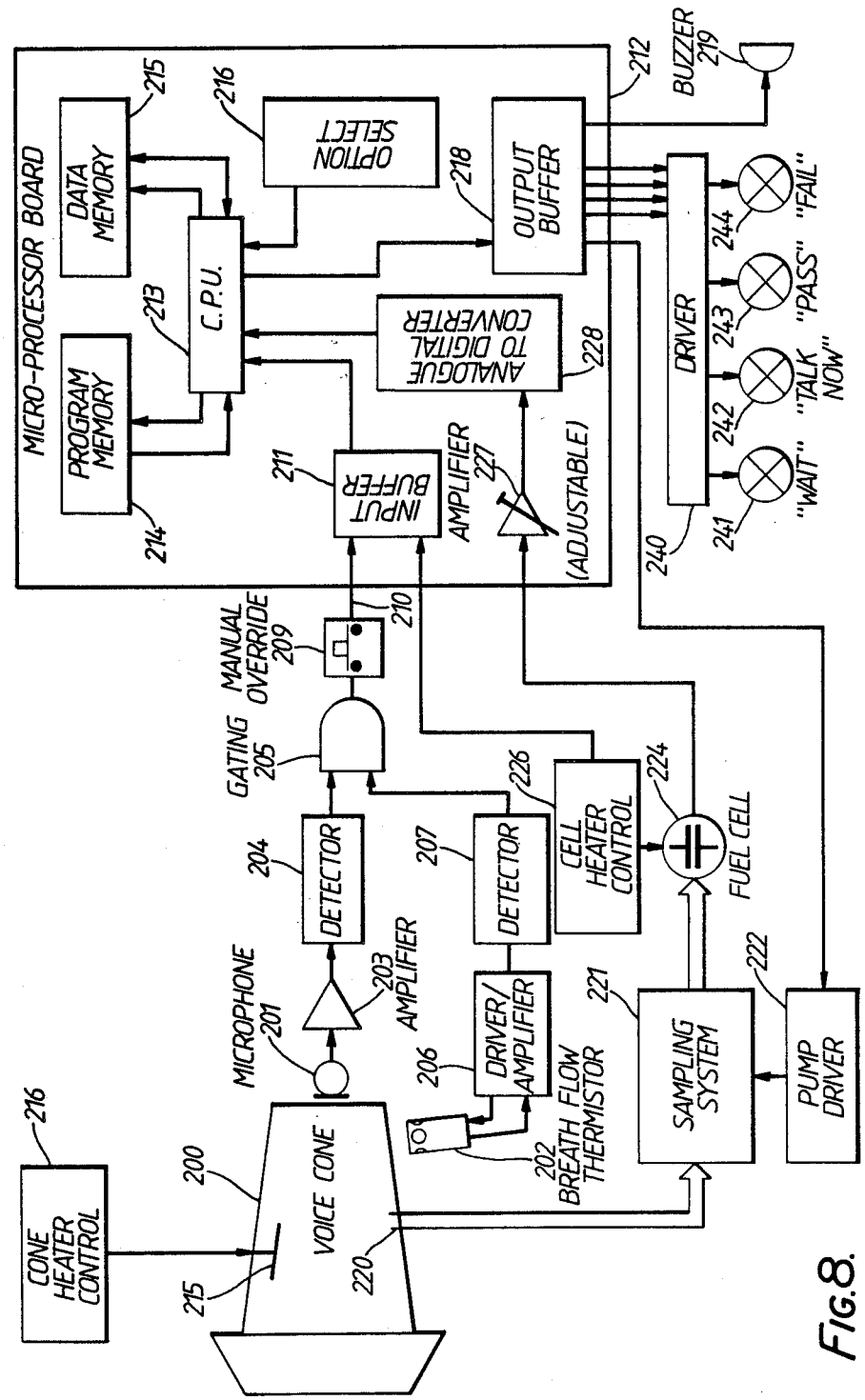
Figure 11:
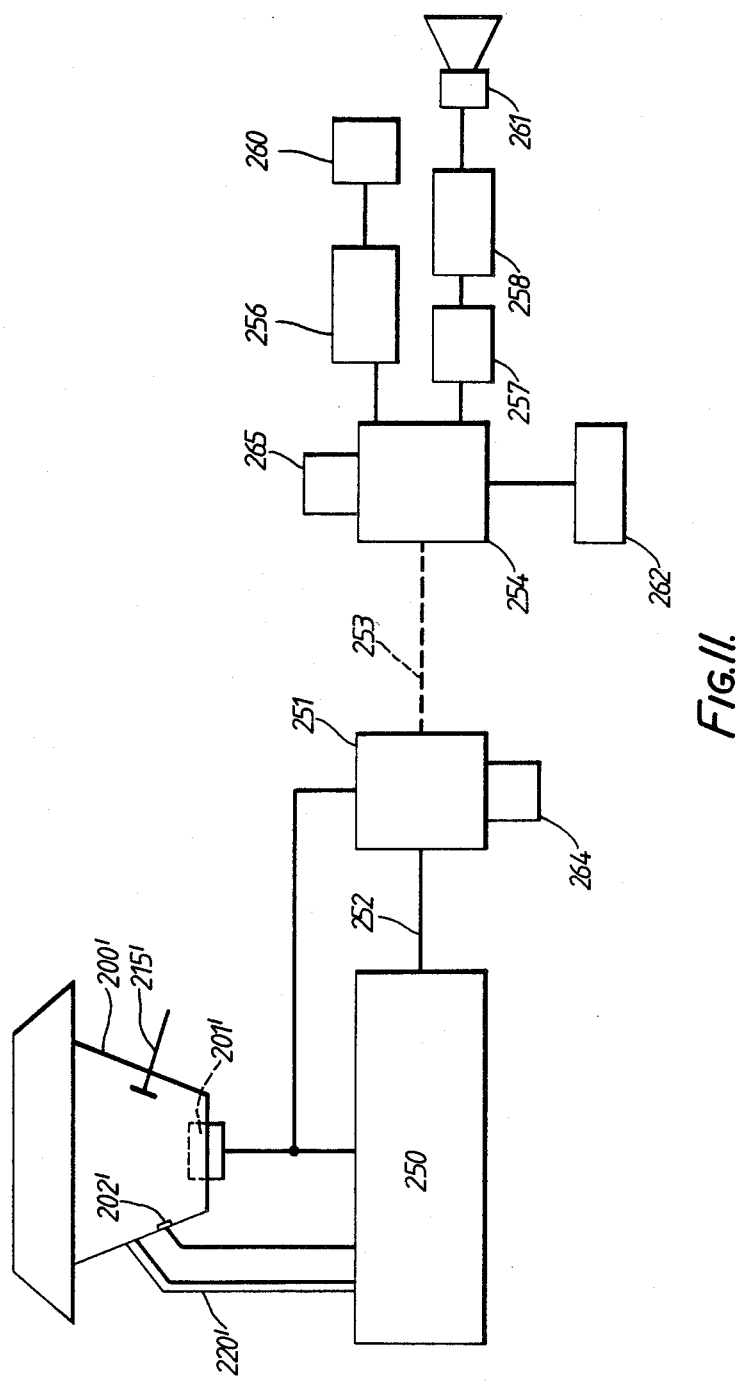

The invention may be performed in various ways and one embodiment with some possible modifications will now be described by way of example with reference to the accompanying drawings, in which:

FIG. 1 is a block diagram illustrating the main components of the first example, FIG. 2 is a block diagram schematically illustrating the triggering circuit, FIG. 3 is a block diagram illustrating the sampling circuit, FIG. 4 is a block diagram illustrating the cell heating circuit, FIG. 5 is a block diagram illustrating the "battery low" circuit, FIG. 6 is a block diagram illustrating the cell voltage measurement circuit, FIG. 7 is a block diagram illustrating the resetting logic circuit, FIG. 8 is a block diagram illustrating another embodiment including a microphone and thermister proximity detector, FIG. 9 is a block diagram illustrating the logic components of the microphone and thermister detector of FIG. 8, FIG. 10 is a sectional side elevation illustrating the speech cone housing the microphone and thermistor, and FIG. 11 is a diagram illustrating another embodiment.

The first example is illustrated diagrammatically in FIG. 1 and in this the instrument is designed to be installed close to the entry to a sports ground or the like and is intended to detect whether entrants have recently been consuming alcohol in excessive quantities. It includes an alcohol detection system combined with a microphone which will normally be positioned close to a turnstile or entry gate and so arranged that each entrant must speak closely into the microphone before being admitted. The apparatus includes a speech cone 10 open at the front end and including a microphone 11 and a gas sampling conduit 12 leading to a sampling pump 13 controlled by the sampling circuit 14. The sampling pump draws in a gas sample and exposes this to an electrochemical fuel cell 15 whose output is fed to a fuel cell measurement circuit 16 and thence after evaluation to a display or warning indicator 17. A heating circuit 18 is arranged to hold the fuel cell and, if necessary, also the sampling pump system 13 at a preselected temperature. The microphone 11 is electrically coupled to the trigger circuit 20, which is connected to the resetting logic circuit 21 which also has an input from the cell measurement circuit 16 and output connections to the display circuit 17. A battery low circuit 22 indicates a low voltage on the battery and provides an indication that the battery needs to be changed.

The triggering circuit to operate the sampling system is illustrated in FIG. 2. As stated it needs to be fully or semi-automatic in operation and it was felt that a delay has to be introduced in the circuit to allow enough breath to accumulate near the microphone for an adequate sample to be taken. In FIG. 2 the microphone 11 is connected through the amplifier 30 to a voltage comparator 31 having an adjustable level set by rheostat 32. The output of this comparator 31 is fed through gate h to a 1.1 second timer 34 providing a delay signal via gate g to NAND gate e and via the inverter f to the set input T of JK flip flop 36 which produces the initiating output signal on Q−. The trigger may be bypassed by manual switchbutton 37. Thus if at the end of the 1.1 second time interval of timer 34 the output of the comparator 31 is still high, the flip flop 36 is set Q+ high Q− low.

In this example using an electrochemical fuel cell and a motorized pump drawing a sample across the cell enough time must be allowed for the cell output to reach a peak. Accordingly the sampling control circuit illustrated in FIG. 3 includes a cell peak timer 40 and a pump running timer 41. The two timers are triggered by the Q− output of the flip flop 36 such that the pump motor 42 will then run for 0.9 seconds to draw a predetermined volumetric sample over the cell, the pump speed being determined by an adjustable rheostat 43. During the timing period of the timer 40 its output on 44 is high so that the relay 45 is energised through transistor switch 46. The relay removes a short circuit 47 across the cell 15 (see FIG. 6) thus allowing the cell voltage to be evaluated and after 6.5 seconds the output 44 of the timer goes low, a current is pulsed briefly through the comparator 48 and the transistors 49, 50 are turned on sounding the buzzer 51. When the voltage across resistor 52 falls the transistors are turned off.

In this example it is important to provide heating to the electrochemical cell and to maintain its temperature. The heater circuit is illustrated in FIG. 4 where the heater 55 is switched on by transistor 56 under the control of thermistor 57 which is thermally attached to the same disc which carries the heater 55. As the thermistor becomes warmer its resistance decreases and this is applied to comparator 58 to control switch 56 and maintain the heater supply until the thermistor's resistance drops. The heater supply then oscillates on and off around this preselected temperature level and resistor 59 acting through comparator 60 ensures that LED 61 remains on while the heater oscillates.

The battery voltage check circuit is illustrated in FIG. 5 and is based on use of a Zener diode 64 as reference, the series resistor 65 being such as to allow enough current flow to hold the diode at correct voltage. Resistors 66, 67 act as a potential divider and when the voltage between them falls below the predetermined level comparator 68 switch is high and turns on transistor 69 and the LED indicator 70. Hysterisis is provided by the resistors 71, 72.

The cell voltage measurement or evaluation circuit is illustrated in FIG. 6 and one of the problems involved is to allow the cell appropriate time and conditions to "clear", i.e. to revert to a datum level between readings. The output of the cell 15 is connected to a transresistance amplifier circuit 75, including amplifier 76, in which its output is converted to a voltage and fed to the two comparators 77, 78. When the cell output reaches the level set by comparator 77, the output of that comparator goes low turning on a transistor 79 to drive a limit LED 80. When the cell output reaches the level determined by comparator 78 (which is less than that set by 77) the comparator output at 81 goes low, is inverted by NAND gate 82 and fed into NAND gate 83. The latter also receives a signal on S from the cell clear timer (see FIG. 3). As a result if after 6.5 seconds, as determined by timer 40, the output of cell 15 has reached a predetermined level the timer 85 will be triggered and the output of this is fed through the resetting logic circuit of FIG. 7. As a result the cell 15 is short circuited for at least 24.2 seconds before the next sample can be taken.

Referring to FIG. 7 the resetting logic includes NAND gate 86 having four inputs, S, θ, C and L of which input C is derived from NAND gate 87 connected to the short circuit timer 85. The other inputs are derived from the connections shown in other Figures: S in FIG. 3, θ in FIG. 4, and L in FIG. 6. The output of gate 86 only goes low when:

(a) 6.5 second sampling time is up,
(b) The heater is up to temperature,
(c) The cell is not being cleared, and
(d) The cell level is low enough.

When the output of NAND gate 86 goes low the output of NAND gate 90 goes high and this is connected to the "clock" pin CK of the JK flip flop 36 (see FIG. 2a). The rising edge of clock pulse then sets Q− high and Q+ low which means that when the input on T from the triggering circuit is high the sample can again be taken. The display part of the resetting circuit is arranged so that when one transistor 91 and hence its LED 92, are on the other transistor 93 and its LED 94 are off. One LED signals to "Wait" and the other signals "Ready for a Sample".

In the second embodiment illustrated diagramatically in FIG. 8, the system includes many of the features of the first embodiment with certain additions and modifications. In this example there is a speech cone 200 in which is mounted a microphone 201 and a temperature sensing thermistor 202. The microphone output is fed through amplifier 203 and detector 204 to the AND gate 205, which also receives the signal derived from the thermistor 202 via driver amplifier 206 and detector 207. The gate output which includes a manual override 209, is fed on 210 to the input buffer 211 of the basic microprocessor control circuit 212.

The voice cone 200 is also provided with an internal heater 215 operated and controlled by a thermostatic control unit 216. In addition the voice cone 200 is provided with a small breath sampling inlet 220 leading to a sampling system including a sampling pump 221 driven by a small electric motor 222, the pump being arranged to draw in a breath sample over a predetermined time interval and pass this over an electrochemical fuel cell 224. The cell includes a heater controlled by a thermostatic actuator 226 and the output of the cell is fed through amplifier 227 to the control circuit 212 and in particular to an analogue to digital converter 228. This feeds the output to a central processing unit 213 which is also connected to a program memory 214 and a data memory 215. An option select unit 216 controls the functions of the unit 214. The output of the unit 214 is also connected to the output buffer 218, which has one output to a warning buzzer 219, another output to a driver circuit 240 arranged to actuate information or warning signals 241 to 244 indicating, for example, "Wait", "Talk Now", "Pass" or "Fail".

The circuitry involved in the components of the voice cone 200 is illustrated in more detail in FIG. 9 in which like parts are indicated by the same reference numerals. Here the output of the microphone 201 is fed through an adjustable gain band pass filter 199 to the comparator amplififer 203 and integrator/low pass filter 198 acting as an integrator to a second comparator 197 whose output is connected to the AND gate 205. The other input to the comparators 203 and 197 is a voltage reference signal 196. The breath temperature sensing thermistor 202 is connected across the supply voltage through a constant current source 195 and its output is fed through a capacitor 217, which removes the D.C. component, an adjustable gain rectifier 194, and a low pass filter 193 (which acts in effect as an integrator) to a comparator 192 acting as the detector 207 and having another constant voltage reference input 191.

The actual construction of the speech cone 10 is illustrated in detail in FIG. 10. The cone 10 in this example is formed of aluminium or other light metal and has a mounted flange 180 on its front rim to allow it to be positioned in an opening or socket of a notice board, the cone having a central opening at its rear end in which is fitted the microphone 11. The wall of the cone includes a passage 179 acting as a breath sampling entrance leading to the sampling tube 12 and the cone is also provided with an opening or socket 178 to receive and locate the thermistor 202. Thus it will be seen that when a subject speaks towards the microphone, the speech signal will be processed and fed as one input to the gate circuit 205. If the subject is sufficiently close to the microphone the resulting turbulence in the local air stream adjacent the thermistor 202 will cause fluctuations in the thermistor output which when processed by 217, 194 and 193 will be fed as the other input to the gate circuit to act in effect as a "presence signal". It will be noted that the thermistor signal fed to the gate is in this way independent of ambient temperature and is acting as a turbulence detector rather than an air temperature sensor.

As mentioned above the invention may also be applied to situations in which an individual is required to speak into a microphone and at the same time to be subjected to a test for alcohol or drugs in the expired breath. This may be of particular value, for example, in cases of "home arrest" or "parole", or the like. In essence the subject is required to speak into a microphone which is coupled via a telephone system or radio transmitter-receiver link to a remote monitoring unit, and the microphone is associated with an alcohol or drug detecting system, as described for example in one of the previous embodiments. The output of the alcohol detector is fed into the same remote transmission system as the microphone output so that the remote receiver receives both a speech signal and an alcohol detection or level signal.

In the system illustrated diagrammatically in FIG. 11 parts similar to components of previous examples are indicated by the same reference numerals with added suffixes. The apparatus includes a voice cone 200' which incorporates a microphone 201' and heater 215' and has a gas sampling inlet 220' and thermistor 202'. The outputs from the microphone, gas sampler, and thermistor, are incorporated into a control circuit 250, which includes most of the components illustrated, for example, in FIG. 8. In this instance the output of the microphone 201' is also fed to a transmitter unit 251, which additionally has an input 252 from the processing circuitry 250, this input 252 carrying a signal which indicates or represents the presence or quantity of detected alcohol in the breath. The transmitter 251, which may be part of a telephone system or, for example, a radio link, is coupled via the link indicated diagrammatically at 253 to a remote receiver unit 254 which is associated with a number of filters or identifying circuits 256, 257, 258. The filter 256 is arranged to extract or separate from the combined input just the information concerning the presence or quantity of alcohol detected and this is displayed or recorded by the indicator unit 260. Filter 257 separates out the speech component of the combined signal reaching the receiver 254 and this is fed to a voice identification unit 258 containing filters of known type designed to provide an indication that the frequency pattern of the received speech complies with a known pattern previously obtained for that individual subject. The speech signal is transmitted to the loudspeaker 261 and the receiving station may also include an associated microphone 262 to permit two-way speech between the two remote stations. As a possible alternative or addition the system may include an identify card recognition unit 264 coupled to the transmitter 251 and an identity recognition unit 265 at the receiver station to provide an indication that the correct card has been inserted.

Thus by means of some or all of these recognition devices, it is possible for a police officer or other person at the remote station to obtain reasonably accurate information concerning the presence and identity of the subject speaking into the cone 200' and simultaneously with the transmitted speech there is provided a signal representing the alcohol or drug level in the subject's breath.

I claim:
1. Apparatus for detecting the presence of alcohol in expired breath, from a subject, in the atmosphere, comprising a gas sampler, a detector for the presence of alcohol in a gas sample, an output indicator or recorder coupled to the detector to provide an output signal when alcohol is detected, a presence sensor for sensing the presence of a subject in relation to the gas sampler, and an automatic controller for actuating the sampler and detector in response to a signal from a presence sensor.

2. Apparatus according to claim 1, in which the sensor is responsive to noise level, or variation, or movement, temperature, mass, pressure body weight, or an interruption in a radiated beam, or a combination of two or more such "proximity" or "presence " parameters.

3. Apparatus according to claim 1 in which the sensor includes a microphone responsive to speech.

4. Apparatus according to claim 1, in which the presence sensor is sensitive to movement or turbulence in the air adjacent to the sensor.

5. Apparatus according to claim 1, in which the alcohol detector comprises an electrochemical fuel cell and means for measuring or detecting the output of the cell to provide an indication of the alcohol content in the sample.

6. Apparatus according to claim 1, in which the gas sampler comprises a pump for drawing or impelling a gas sample into contact with the detector.

7. Apparatus according to claim 6, in which the pump is electrically operated, and including a control circuit incorporating a pump running timer.

8. Apparatus according to claim 1, in which the gas sampler and/or detector incorporates a heater and a temperature control.

9. Apparatus according to claim 1, in which the detector is an electrochemical fuel cell.

10. Apparatus according to claim 9, including means for short circuiting the cell between tests.

11. Apparatus according to claim 9, in which the microphone and temperature detector are both located in or adjacent to a cone or cup designed as a microphone mouthpiece.

12. Apparatus according to claim 1, in which the presence sensor includes a microphone acting as an acoustic transducer sensitive to speech, and a temperature responsive element located immediately adjacent thereto, the microphone and temperature sensing element being coupled through logic circuitry to the output.

13. Apparatus for detecting the presence of drugs in the expired breath, from a subject, in the atmosphere, comprising a gas sampler, a detector for the presence of drugs in a gas sample, an output indicator or recorder coupled to the detector to provide an output signal when drugs are detected, a presence sensor for sensing the presence of a subject in relation to the gas sampler, and an automatic controller for actuating the sampler and detector in response to a signal from a presence sensor.

14. Apparatus for detecting the presence of alcohol in the expired breath, from a subject, in the atmosphere, comprising a gas sampler, a detector for the presence of alcohol in a gas sample, an output indicator or recorder coupled to the detector to provide an output signal when alcohol is detected, an acoustic transducer sensitive to speech and providing a basic speech signal and a proximity or presence sensor sensitive to the presence of an adjacent human body and producing a proximity signal or modulation, and means for detecting a simultaneous or concurrent combination of speech and presence, and an automatic controller for actuating the sampler and detector in response to the detection of the combination of speech and presence.

15. Apparatus according to claim 14, in which the proximity sensor is a temperature responsive element positioned close to the acoustic transducer.

16. Apparatus for detecting the presence of drugs in the expired breath, from a subject, in the atmosphere, comprising a gas sampler, a detector for the presence of drugs in a gas sample, an output indicator or recorder coupled to the detector to provide an output signal when drugs are detected, an acoustic transducer sensitive to speech and providing a basic speech signal and a proximity or presence sensor sensitive to the presence of an adjacent human body and producing a proximity signal or modulation, and means for detecting a simultaneous or concurrent combination of speech and presence, and an automatic controller for actuating the sampler and detector in response to the detection of the combination of speech and presence.

17. Apparatus according to claim 16, in which the proximity sensor is a temperature responsive element positioned close to the acoustic transducer.

18. Apparatus for detecting the presence of alcohol in the expired breath, from a subject, in the atmosphere comprising a gas sampler, a detector for the presence of alcohol in a gas sample, an output indicator or recorder coupled to the detector to provide an output signal when alcohol is detected, a microphone responsive to speech and an automatic controller for actuating the sampler and detector in response to the subject's speech being detected by the microphone.

19. Apparatus for detecting the presence of drugs in the expired breath, from a subject, in the atmosphere comprising a gas sampler, a detector for the presence of drugs in a gas sample, an output indicator or recorder coupled to the detector to provide an output signal when drugs are detected, a microphone responsive to speech and an automatic controller for actuating the sampler and detector in response to the subject's speech being detected by the microphone.

* * * * *

REEXAMINATION CERTIFICATE (2296th)
United States Patent [19]
Jones

[11] B1 4,868,545
[45] Certificate Issued May 10, 1994

[54] ALCOHOL OR DRUGS BREATH DETECTING DEVICES

[75] Inventor: Thomas P. Jones, Sully, United Kingdom

[73] Assignee: Lion Technology Limited, Barry, England

Reexamination Request:
No. 90/003,152, Aug. 5, 1993

Reexamination Certificate for:
Patent No.: 4,868,545
Issued: Sep. 19, 1989
Appl. No.: 154,252
Filed: Jan. 28, 1988

[22] PCT Filed: Jun. 12, 1987
[86] PCT No.: PCT/GB87/00412
§ 371 Date: Jan. 28, 1988
§ 102(e) Date: Jan. 28, 1988
[87] PCT Pub. No.: WO87/07723
PCT Pub. Date: Dec. 17, 1987

[30] Foreign Application Priority Data
Jun. 14, 1986 [GB] United Kingdom ............... 8614515

[51] Int. Cl.$^5$ ............................................. G08B 23/00
[52] U.S. Cl. ................................. 340/573; 73/23.3

[56] References Cited
U.S. PATENT DOCUMENTS
4,617,821 10/1986 Yokoyama et al. .............. 73/23.3
4,665,385 5/1987 Henderson ....................... 340/539

*Primary Examiner*—Glen R. Swann, III

[57] ABSTRACT

Apparatus for detecting the presence of alcohol in expired breath in the atmosphere, comprising a gas sampler, a detector for the presence of alcohol in a gas sample, an output indicator or recorder coupled to the detector to provide an output signal when alcohol is detected, and an automatic controller for actuating the sampler and detector in response to a signal from a sensor arranged to be responsive to the presence of a subject to be tested.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-19 is confirmed.

* * * * *